(12) United States Patent
Tsujita et al.

(10) Patent No.: US 9,861,340 B2
(45) Date of Patent: Jan. 9, 2018

(54) ULTRASOUND PROBE

(71) Applicant: FUJIFILM Corporation, Minato-ku, Tokyo (JP)

(72) Inventors: Kazuhiro Tsujita, Ashigarakami-gun (JP); Takeya Abe, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 66 days.

(21) Appl. No.: 13/948,697

(22) Filed: Jul. 23, 2013

(65) Prior Publication Data

US 2013/0310694 A1 Nov. 21, 2013

Related U.S. Application Data

(63) Continuation of application No. PCT/JP2012/000778, filed on Feb. 6, 2012.

(30) Foreign Application Priority Data

Feb. 7, 2011 (JP) .................................. 2011-023733
Jan. 30, 2012 (JP) .................................. 2012-016061

(51) Int. Cl.
*A61B 8/14* (2006.01)
*A61B 8/00* (2006.01)
(Continued)

(52) U.S. Cl.
CPC .......... *A61B 8/4444* (2013.01); *A61B 5/0059* (2013.01); *A61B 5/0095* (2013.01);
(Continued)

(58) Field of Classification Search
CPC .................. A61B 1/00167; A61B 1/07; A61B 2019/5206; A61B 5/0095; A61B 5/0059
(Continued)

(56) References Cited

U.S. PATENT DOCUMENTS 4,538,618 A * 9/1985 Rosenberg et al. ........... 600/407
5,033,814 A 7/1991 Brown et al.
(Continued)

FOREIGN PATENT DOCUMENTS

JP 3-279908 A 12/1991
JP 9-264839 A 10/1997
(Continued)

OTHER PUBLICATIONS

Communication dated Sep. 8, 2015, issued by the Japan Patent Office in corresponding Japanese Application No. 2014-223995.
(Continued)

*Primary Examiner* — Ellsworth Weatherby
(74) *Attorney, Agent, or Firm* — Sughrue Mion, PLLC (57) ABSTRACT

An optical fiber guides light output from a light source to an ultrasound probe. The ultrasound probe includes a light guiding section that guides the light from a light input end, which is optically coupled with the optical fiber to a light output end provided in the vicinity of ultrasonic transducers. The light guiding section has a first light guiding portion that includes the light input end, and a second light guiding portion that includes the light output end. The first light guiding portion is formed by glass, and magnifies input light. The second light guiding portion is formed by resin, and emits the light toward a subject from the light output end.

12 Claims, 4 Drawing Sheets

(51) Int. Cl.
*A61B 5/00* (2006.01)
*G01N 29/24* (2006.01)

(52) U.S. Cl.
CPC .......... *A61B 8/4416* (2013.01); *A61B 8/4455* (2013.01); *G01N 29/2418* (2013.01); *A61B 5/0035* (2013.01); *G01N 2291/02475* (2013.01)

(58) Field of Classification Search
USPC .................................................. 600/407, 459
See application file for complete search history.

(56) References Cited

U.S. PATENT DOCUMENTS

| | | | |
|---|---|---|---|
| 6,690,958 B1 * | 2/2004 | Walker | A61B 5/14542 600/309 |
| 6,819,861 B2 * | 11/2004 | Ota | G02B 6/08 250/227.31 |
| 6,979,292 B2 * | 12/2005 | Kanayama et al. | 600/437 |
| 7,860,360 B2 * | 12/2010 | Rockwell | G02B 6/1245 385/28 |
| 2005/0187471 A1 * | 8/2005 | Kanayama et al. | 600/437 |
| 2006/0184042 A1 | 8/2006 | Wang et al. | |
| 2007/0244371 A1 * | 10/2007 | Nguyen et al. | 600/300 |
| 2007/0249916 A1 * | 10/2007 | Pesach | A61B 5/0095 600/316 |
| 2009/0005685 A1 * | 1/2009 | Nagae | A61B 5/0059 600/459 |
| 2010/0094134 A1 * | 4/2010 | Zhu | A61B 5/0073 600/473 |
| 2010/0229650 A1 | 9/2010 | Shahzad et al. | |
| 2010/0256496 A1 * | 10/2010 | Zhu | 600/459 |
| 2011/0066023 A1 | 3/2011 | Kanayama et al. | |
| 2011/0085348 A1 * | 4/2011 | Dobson | 362/551 |
| 2011/0112391 A1 * | 5/2011 | Nishihara et al. | 600/407 |
| 2011/0178401 A1 | 7/2011 | Ichihara et al. | |
| 2011/0201914 A1 | 8/2011 | Wang et al. | |
| 2012/0318066 A1 | 12/2012 | Ichihara et al. | |
| 2013/0197345 A1 | 8/2013 | Nagae et al. | |
| 2013/0310694 A1 | 11/2013 | Tsujita et al. | |
| 2014/0051966 A1 | 2/2014 | Irisawa | |
| 2014/0051967 A1 | 2/2014 | Irisawa | |
| 2014/0350368 A1 | 11/2014 | Irisawa | |
| 2015/0133765 A1 | 5/2015 | Ichihara et al. | |
| 2016/0157730 A1 | 6/2016 | Irisawa | |

FOREIGN PATENT DOCUMENTS

| | | |
|---|---|---|
| JP | 2005-218684 A | 8/2005 |
| JP | 2009-31268 A | 2/2009 |
| JP | 2010-012295 A | 1/2010 |
| JP | 2010-125260 A | 6/2010 |
| JP | 2010-179085 A | 8/2010 |
| JP | 2010167167 A | 8/2010 |
| JP | 2011-501150 A | 1/2011 |
| JP | 2011229609 A | 11/2011 |
| JP | 2012179350 A | 9/2012 |
| JP | 2012-228401 A | 11/2012 |
| JP | 2012-228402 A | 11/2012 |
| WO | 2010/005116 A1 | 1/2010 |
| WO | 2010005109 A1 | 1/2010 |
| WO | 2013/128922 A1 | 9/2013 |

OTHER PUBLICATIONS

Communication dated Apr. 8, 2016 from the European Patent Office in counterpart Application No. 12744556.7.
Communication dated Apr. 5, 2016 from Japanese Patent Office in counterpart Application No. 2014-223995.
Communication dated Nov. 11, 2016 from the European Patent Office in counterpart European application No. 12744556.7.
Communication dated Jul. 17, 2017, from the European Patent Office in counterpart European application No. 12744556.7.

* cited by examiner

FIG.7
ENERGY DENSITY AND LIGHT GUIDING PLATE LENGTH

LIGHT DIFFUSING SURFACE

FIG.10

ULTRASOUND PROBE

TECHNICAL FIELD

The present invention is related to an ultrasound probe. More specifically, the present invention is related to an ultrasound probe which is employed in photoacoustic imaging.

The ultrasound examination method is known as an image examination method that enables examination of the state of the interior of living organisms in a non invasive manner. Ultrasound examination employs an ultrasound probe capable of transmitting and receiving ultrasonic waves. When the ultrasonic waves are transmitted to a subject (living organism) from the ultrasound probe, the ultrasonic waves propagate through the interior of the living organisms, and are reflected at interfaces among tissue systems. The ultrasound probe receives the reflected ultrasonic waves and images the state of the interior of the subject, by calculating distances based on the amounts of time that the reflected ultrasonic waves return to the ultrasound probe.

Photoacoustic imaging, which images the interiors of living organisms utilizing the photoacoustic effect, is also known. Generally, in photoacoustic imaging, pulsed laser beams such as laser pulses are irradiated into living organisms. Biological tissue that absorbs the energy of the pulsed laser beams generates ultrasonic waves (photoacoustic signals) by volume expansion thereof due to heat. An ultrasound probe or the like detects the photoacoustic signals, and constructs photoacoustic images based on the detected signals, to enable to enable visualization of the living organisms based on the photoacoustic signals.

In photoacoustic imaging, there are cases in which a pulsed laser beam is guided from a laser light source to an ultrasound probe, and the pulsed laser beam is emitted from a light emitting section provided on the ultrasound probe. An ultrasound probe equipped with a light emitting section is disclosed in Japanese Unexamined Patent Publication No. 2010-012295, for example. In the invention of Japanese Unexamined Patent Publication No. 2010-012295, a plurality of optical fibers are employed to guide light from a laser light source to an ultrasound probe. The output ends of the optical fibers constitute the light emitting section that emits light onto a subject. In the invention of Japanese Unexamined Patent Publication No. 2010-012295, a plurality of ultrasonic transducers that transmit and/or detect ultrasonic waves are arranged in a single dimension with predetermined intervals among the transducers. The output ends of the fibers, which are light emitting portions, are arranged in the gaps among adjacent ultrasonic transducers.

DISCLOSURE OF THE INVENTION

In the invention of Japanese Unexamined Patent Publication No. 2010-012295, the output ends of the optical fibers emit light toward the subject. Light is concentrated at the output ends of the optical fibers, which are thin, and the energy density of light at the output ends becomes high. In the invention of Japanese Unexamined Patent Publication No. 2010-012295, it is necessary to reduce the emitted amount of light, in order to emit light at an energy density that satisfies safety standards with respect to living organisms (20 mJ/cm$^2$ for light having a wavelength of 500 nm, for example). Because the amount of light emitted by each optical fiber is limited in this manner, it becomes necessary to increase the number of optical fibers in order to emit a sufficient amount of light while satisfying the safety standards. In addition, the optical fibers are arranged with predetermined intervals therebetween in the invention of Japanese Unexamined Patent Publication No. 2010-012295, and fluctuations arise in the amounts of light emitted at portions directly under optical fibers and portions under the spaces among adjacent optical fibers. Therefore, light cannot be uniformly emitted onto an area to be illuminated.

The present invention has been developed in view of the foregoing circumstances. It is an object of the present invention to provide an ultrasound probe having an illumination system capable of emitting a sufficient amount of light onto a wide illumination area.

To achieve the above objective, the present invention provides an ultrasound probe, comprising:

a plurality of ultrasonic transducers which are arranged along a predetermined direction;

an optical fiber that guides light emitted from a light source to a probe main body; and light guiding means that guides light from a light input end which is optically coupled with the optical fiber to a light output end provided in the vicinity of the ultrasonic transducers;

the light guiding means including:

a first light guiding portion formed by a glass material that includes the light input end and guides light from the light input end toward the light output end and that enlarges the cross sectional area of input light at the light input end at an output end of the first light guiding portion; and a second light guiding portion formed by a resin material that includes the light output end, guides light guided by the first light guiding portion to the light output end, and emits light from the light output end toward a subject.

The present invention may adopt a configuration, wherein:

the first light guiding portion includes a light guiding path formed in a tapered shape.

The present invention may adopt a configuration, wherein:

the first light guiding portion enlarges the width of guided light in the predetermined direction at an output end of the first light guiding portion to be at least greater than the width of the input light in the predetermined direction at the light input end.

The present invention may adopt a configuration, wherein:

the second light guiding portion is curved in a direction toward the interiors of the ultrasonic transducers.

Alternatively, the present invention may adopt a configuration, wherein:

the light guiding means is provided inclined at a predetermined angle with respect to ultrasonic wave detecting surfaces of the ultrasonic transducers.

The ultrasound probe may be provided with a plurality of the optical fibers and a plurality of the light guiding means. In this case, a configuration may be adopted, wherein the plurality of light guiding means are arranged along the predetermined direction. The plurality of light guiding means may be arranged along a direction perpendicular to the predetermined direction instead of or in addition to being arranged in the predetermined direction so as to face the ultrasonic transducers which are interposed among the plurality of light guiding means.

Alternatively, the plurality of optical fibers which are arranged along the predetermined direction may be optically coupled to the light input end of a single light guiding means. In this case, two of the light guiding means may be provided; and the two light guiding means may be provided to face each other with the ultrasonic transducers interposed therebetween.

The light guiding means may be a slab shaped light guiding plate having a tabular core and planar cladding layers provided on both surfaces of the tabular core. Alternatively, the light guiding means may comprise a light transmitting portion having light transmitting properties and reflective members which are formed to sandwich the light transmitting portion therebetween.

In the ultrasound probe of the present invention, it is preferable for the distance from the light input end to the boundary between the first light guiding portion and the second light guiding portion to be 8 mm or greater.

The ultrasound probe of the present invention may further comprise:

an adapter that transmits light and ultrasonic waves, which is mounted to the ultrasound probe so as to cover the ultrasonic wave detecting surfaces of the ultrasonic transducers and the light output end of the light guiding means.

A configuration may be adopted, wherein the ultrasound probe of the present invention further comprises:

a diffusion plate that diffuses light at the light output side of the light output end.

Alternatively, a configuration may be adopted, wherein:

a diffusing surface that diffuses light is formed on at least one of the end surface at the light output side of the second light guiding portion and the end surface of the second light guiding portion at the boundary between the first light guiding portion and the second light guiding portion.

The ultrasound probe of the present invention couples the light guiding means to the output ends of the optical fibers that guide light to a probe main body, employs the light guiding means to guide the light to the vicinity of the ultrasonic transducers, and emits light to a subject from the vicinity of the ultrasonic transducers. The light guiding means includes the first light guiding portion and the second light guiding portion. The first light guiding portion enlarges the cross sectional area of light to be greater than that at the light input end. Thereby, light emission onto a greater area compared to a case in which light is emitted from the output ends of optical fibers is enabled, from the light output end having a larger area than the output ends of optical fibers. In addition, the energy density of light at the light output end can be decreased compared to the energy density of light at the light input end. For these reasons, the amount of light which is input into optical fibers can be increased compared to a case in which light is emitted onto a subject from the output ends of optical fibers, and light emission with a sufficient amount of light while satisfying safety standards becomes possible.

BEST MODE FOR CARRYING OUT THE INVENTION

Figure 1:
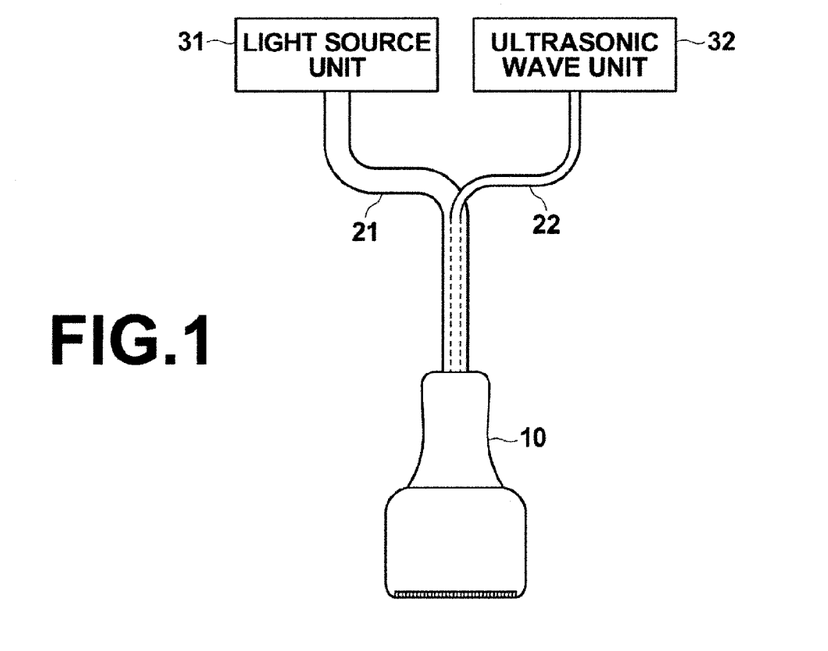
FIG. 1 is a block diagram that illustrates a photoacoustic image diagnosis apparatus that includes an ultrasound probe according to a first embodiment of the present invention.

Hereinafter, embodiments of the present invention will be described in detail with reference to the attached drawings. FIG. 1 illustrates a photoacoustic image diagnosis apparatus that includes an ultrasound probe according to a first embodiment of the present invention. The photoacoustic image diagnosis apparatus includes: an ultrasound probe 10; a light source unit 31; and an ultrasonic wave unit 32. The ultrasound probe 10 includes: a light emitting section that emits light onto subjects; and ultrasonic transducers which are capable at least of detecting ultrasonic waves from subjects. The light source unit 31 is a laser unit that generates pulsed laser beams, for example, and generates light to be emitted onto subjects by the ultrasound probe 10. The ultrasonic wave unit 32 generates photoacoustic images based on ultrasonic wave signals detected by the ultrasound probe 10.

The ultrasound probe 10 includes: an array portion, in which a plurality of ultrasonic transducers are arranged in a predetermined direction; and a grip portion which is held by an operator when utilizing the probe, for example. The arrangement of the ultrasonic transducers may be one dimensional or two dimensional. The ultrasound probe 10 is connected to the light source unit 31 via optical fibers 21. The optical fibers 21 include a plurality of optical fibers, for example. The pulsed laser beam generated by the light source unit is guided to the ultrasound probe 10 by the optical fibers 21, and emitted onto a subject from the light emitting section of the ultrasound probe 10. In addition, the ultrasound probe 10 is connected to the ultrasonic wave unit 32 via an electrical cable 22.

Figure 2A:
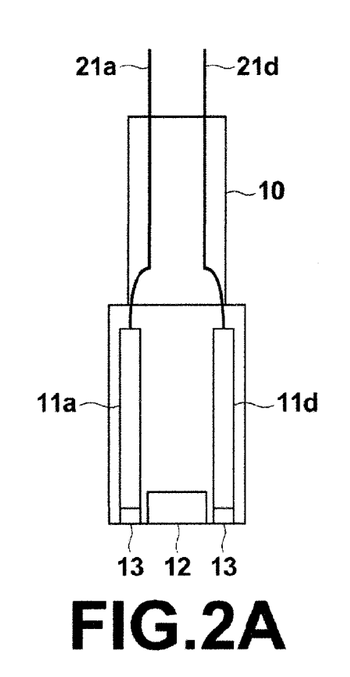
FIG. 2A is a sectional diagram of the ultrasound probe in the lateral direction.
Figure 2B:
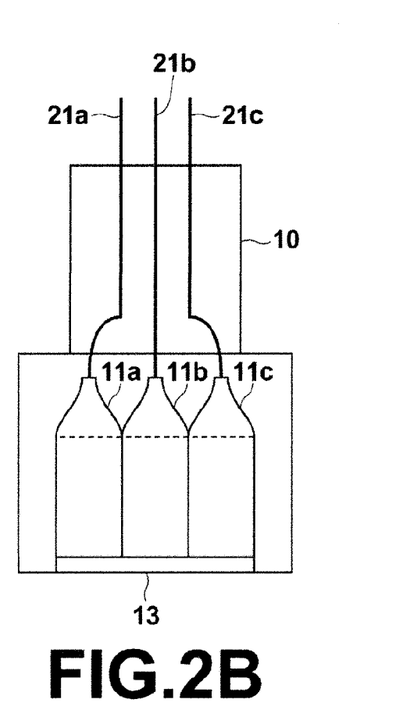
FIG. 2B is a sectional diagram of the ultrasound probe in the frontal direction.

FIG. 2A is a sectional view of the ultrasound probe 10 in the lateral direction, and FIG. 2B is a sectional view of the ultrasound probe 10 in the frontal direction. Note that the electrical cable 22 is omitted in FIG. 2A and FIG. 2B. As illustrated in FIG. 2A, the ultrasound probe 10 has ultrasonic transducers 12 on the surface thereof toward the side that contacts a subject. Light guiding plates (light guiding means) 11a and 11d that form light guiding paths or wave guiding paths are provided at both sides of the ultrasonic transducers 12. A light input end of the light guiding plate 11a is optically coupled with an optical fiber 21a, and a light input end of the light guiding plate 11d is optically coupled with an optical fiber 21d. Quartz fibers or hollow fibers may be employed as the optical fibers 21a and 21d. Bundled fibers, in which a plurality of optical fibers are bundled, may also be employed as the optical fibers 21a and 21d.

The surfaces of the light guiding plates 11a and 11d opposite the light input ends thereof constitute light output ends. The light output ends are provided in the vicinity of the ultrasonic transducers. The light guiding plates 11a and 11d guide light input into the light input ends thereof to the light output ends thereof. The light guiding plates 11a and 11d are slab shaped light guiding plates having tabular cores and planar cladding layers provided on both surfaces of the tabular cores. The refractive indices of the cores and the cladding layers are different. Therefore, total reflection occurs at the boundaries between the cores and the cladding layers, and light propagates therethrough with substantially no loss. Alternatively, reflective films may be coated on the tabular cores, to guide light waves, or light waves may be guided by total reflection caused due to differences in refractive indices between the cores and air. Light diffusing plates 13 are provided at the light output ends of the light guiding plates 11a and 11d. The light output surfaces of the light diffusing plates 13 constitute the light emitting section of the ultrasound probe 10.

The light guiding plates 11a and 11d face each other in a direction perpendicular to the direction in which the ultrasonic transducers 12 are arranged, with the ultrasonic transducers interposed therebetween. As illustrated in FIG. 2B, three light guiding plates 11a through 11c that include the light guiding plate 11a are provided on the side of the ultrasonic transducers 12 at which the light guiding plate 11a is provided. The light guiding plates 11a through 11c are arranged along the direction in which the ultrasonic transducers 12 are arranged. An optical fiber 21b is optically coupled with the light guiding plate 11b, and an optical fiber 21c is optically coupled with the light guiding plate 11c. Although not illustrated in FIG. 2B, three light guiding plates that include the light guiding plate 11d are provided on the ultrasonic transducers 12 at which the light guiding plate 11d is provided. These three light guiding plates are also arranged along the direction in which the ultrasonic transducers 12 are arranged, and are optically coupled to corresponding optical fibers.

Figure 3:
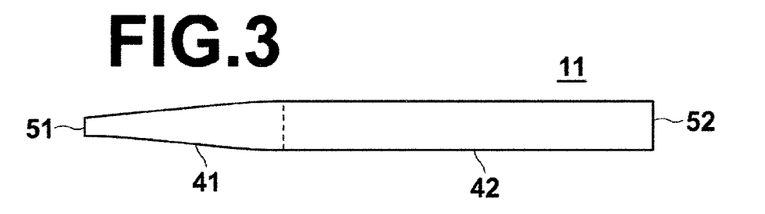
FIG. 3 is a light guiding plate viewed from the lateral surface thereof.

FIG. 3 is a diagram that illustrates a light guiding plate 11. In FIG. 3, the light guiding plate 11 is illustrated as viewed from the lateral direction (the same direction as FIG. 2A). The light guiding plate 11 has: a first light guiding portion 41 that includes a light input end 51; and a second light guiding portion 42 that includes a light output end 52. The first light guiding portion 41 guides light input into the light input end 51 toward the light output end 52. The second light guiding portion 42 guides the light guided thereto by the first light guiding portion 41 to the light output end 52.

The first light guiding portion 41 is formed by a glass material. The first light guiding portion 41 includes a light guiding path which is formed as a tapered shape, for example. The first light guiding portion 41 enlarges the cross sectional area of light at a light output end of the first light guiding portion 41 compared to the cross sectional area of light input at the light input end 51. For example, the first light guiding portion 41 enlarges the width of guided light in the direction in which the ultrasonic transducers are arranged at the output end of the first light guiding portion 41 to be at least greater than the width of the input light in the direction in which the ultrasonic transducers are arranged at the light input end 51. Meanwhile, the second light guiding portion 42 is formed by a resin material, such as acryl. The second light guiding portion 42 emits light toward a subject from the light output end 52.

Light output by the light source unit 31 (FIG. 1) propagates through the optical fibers 21 and is guided to the ultrasound probe 10. The optical fibers 21 include a plurality of optical fibers, and each optical fiber is optically coupled with the light input end 51 (FIG. 3) of a light guiding plate 11 corresponding thereto. The light that enters the light guiding plates 11 through the light input ends 51 propagates through the first light guiding portions 41, which are formed into tapered shapes, while enlarging the range of light. The light which has passed through the first light guiding portions 41 enter the second light guiding portions 42, and is guided to the light output ends 52. The guided light is emitted onto the subject from the light output end 52 via the light diffusing plates 13 (FIG. 2A and FIG. 2B).

In the present embodiment, the light guiding plates 11 are coupled to the output ends of the optical fibers that guide light to the probe main body, the light guiding plates 11 are employed to guide light to the vicinity of the ultrasonic transducers, and light is emitted onto the subject from the vicinity of the ultrasonic transducers, instead of emitting light directly toward the subject from the output ends of the optical fibers. The light guiding plates 11 include the first light guiding portions 41 and the second light guiding portions 42. The first light guiding portions 41 enlarge the cross sectional area of light to be greater than that at the light input ends 51. Therefore, light can be emitted from a greater area compared to a case in which light is emitted from the output ends of optical fibers. In addition, the energy density of light at the output side can be reduced compared to the energy density of light at the light input ends 51 for the amount of increase in the light emission area. For this reason, the amount of light caused to enter the optical fibers can be increased compared to a case in which light is emitted onto a subject from the output ends of optical fibers, and a sufficient amount of light can be emitted while satisfying safety standards.

In the present embodiment, the light guiding plates 11 increase the width of light in the direction in which the ultrasonic transducers 12 are arranged. If light is emitted from optical fibers without employing the light guiding plates 11, the light will be emitted discretely in the direction in which the ultrasonic transducers are arranged. Therefore, portions directly under the optical fibers will be illuminated with large amounts of light, while portions among adjacent optical fibers will be illuminated with smaller amounts of light. Because the present embodiment increases the width of light in the direction in which the ultrasonic transducers 12 are arranged, light can be emitted over a wide range in the direction in which the ultrasonic transducers 12 are arranged from a single optical fiber. For this reason, fluctuations in the amounts of light emitted in the direction that the ultrasonic transducers 12 are arranged are resolved compared to cases in which optical fibers directly emit light. Therefore, light can be uniformly emitted onto a wide area to be illuminated.

Here, in order to increase the amount of light which is output from the light output ends 52, it is necessary to cause a greater amount of light to enter the optical fibers, and the energy density increases at the light output ends of the optical fibers and at the light input ends 51. If the energy density at these locations becomes great, there is a possibility that the light input ends 51 will be damaged. Therefore, the first light guiding portions 41 that include the light input ends 51 are formed by a glass material in the present embodiment. Damage to the light input ends 51 (the first light guiding portions 41) can be prevented even when light enters the light input ends 51 at a high energy density, by employing glass as the material thereof. Meanwhile, the second light guiding portions 42 are formed by a resin material in the present embodiment. Resin materials are advantageous in that they are easily processed.

Figure 4A:
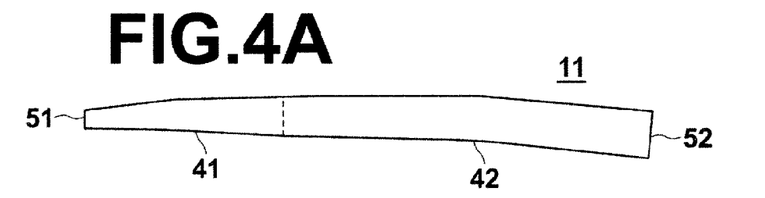
FIG. 4A is a diagram that illustrates an example of an alternate light guiding plate.
Figure 4B:
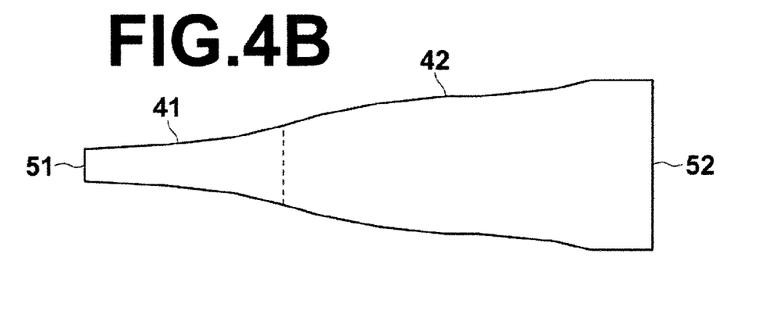
FIG. 4B is a diagram that illustrates another example of an alternate light guiding plate.

FIG. 4A and FIG. 4B illustrate an example of a modified light guiding plate 11. In FIG. 4A, the light guiding plate 11 is illustrated as viewed from the lateral direction (the same direction as FIG. 2A). In FIG. 4B, the light guiding plate 11 is illustrated as viewed from the frontal direction (the same direction as FIG. 2B). As illustrated in FIG. 4A, the second light guiding portion 42 is curved in this example. In addition, as illustrated in FIG. 4B, the second light guiding portion 42 enlarges light in the direction that the ultrasonic transducers are arranged toward the light output end 52. In this case, an advantageous effect that uniformity of light at the light output ends 52 is improved can be expected, compared to a case in which the second light guiding portion 42 is formed in a linear shape (a rectangular plate) as illustrated in FIG. 2B. The first light guiding portion 41 that includes the light input end 51 is the same as that illustrated in FIG. 3.

The second light guiding portion 42 of the light guiding plate 11 illustrated in FIG. 4A and FIG. 4B is curved toward the interior of the ultrasonic transducers within a range that satisfies conditions for total reflection, for example. When light is emitted toward a subject from the sides of the ultrasonic transducers as illustrated in FIG. 2B, there are cases in which it is difficult for light to reach the portion directly under the ultrasonic transducers 12. Employing the light guiding plates 11 which are curved toward the interior of the ultrasonic transducers as illustrated in FIG. 4A to output light in oblique directions from the light output ends 52 facilitates light emission to the portion directly under the ultrasonic transducers 12 from the light guiding plates provided at the sides of the ultrasonic transducers 12. Such three dimensional processing is easy because the second light guiding portions 42 are formed by a resin material.

Note that in FIG. 2A and FIG. 2B, a plurality of combinations of optical fibers and light guiding plates are provided. However, it is not necessary for a plurality of optical fibers and a plurality of light guiding plates to be provided. For example, a configuration may be adopted, wherein a single optical fiber guides light from the light source unit 31 (FIG. 1) to the ultrasound probe 10, and a single light guiding plate 11 provided within the ultrasound probe 10 spreads the width of the light within a range in which the ultrasonic transducers 12 are arranged. In addition, it is not necessary for the plurality of light guiding plates to be provided at both sides of the ultrasonic transducers 12. For example, a configuration may be adopted, wherein a plurality of light guiding plates provided along the arrangement direction of the ultrasonic transducers 12 at a single side of the ultrasonic transducers emit light from the single side of the ultrasonic transducers 12.

Figure 5:
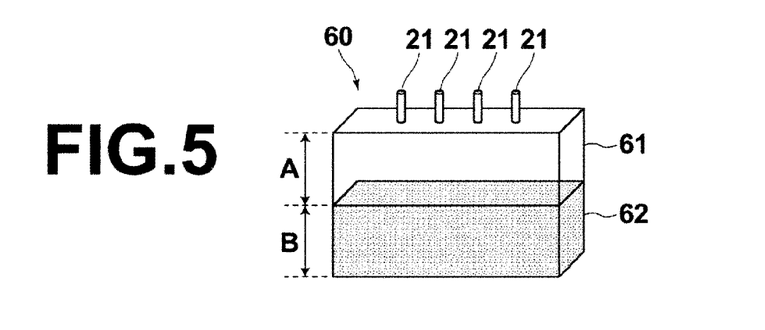
FIG. 5 is a perspective view of a light guiding plate which is employed in an ultrasound probe according to a second embodiment of the present invention.

Next, a second embodiment of the present invention will be described. FIG. 5 illustrates a light guiding plate 60 which is employed in an ultrasound probe according to the second embodiment of the present invention. The light guiding plate 60 of the present embodiment has a first light guiding portion 61 formed by glass and a second light guiding portion 62 formed by resin, in the same manner as the light guiding plate 11 of the first embodiment. In the first embodiment, the three optical fibers 21a through 21c and the three light guiding plates 11a through 11c were coupled to each other, respectively (FIG. 2B). In the present embodiment, a plurality of optical fibers 21 are optically coupled to the light input end of a single light guiding plate 60.

In FIG. 5, the longitudinal direction of the light guiding plate 60 in FIG. 5 corresponds to the direction in which the ultrasonic transducers 12 (FIG. 2A and FIG. 2B) are arranged. Four optical fibers 21 are arranged at equidistant intervals along the arrangement direction of the ultrasonic transducers, for example. The four optical fibers 21 are optically coupled to the light input end of the light guiding plate. The ultrasound probe may be equipped with two light guiding plates 60, which are provided to face each other with the ultrasonic transducers interposed therebetween.

The light guiding plate 60 (the first light guiding portion 61 and the second light guiding portion 62) is formed to be of a parallelepiped shape, for example. The length of the first light guiding portion 61 in the direction in which light is guided is designated as A, and the length of the second light guiding portion 62 in the direction in which light is guided is designated as B. The first light guiding portion 61 guides light that enters thereinto from the side of the light input end to the second light guiding portion 62, while enlarging the cross sectional area of the light. For example, if the length of the first light guiding portion 61 is 11 mm, the fiber core diameters of the optical fibers 21 are 0.3 mm, and the fiber light output has a NA (Numerical Aperture) equivalent to 0.22, the first light guiding portion 61 enlarges the cross sectional area of the light from $\phi 0.3$ mm=$7 \cdot 10^{-4}$ cm$^2$ to $\phi 2.8$ mm=0.062 cm$^2$. The second light guiding portion 62 guides the light guided thereto by the first light guiding portion 61 to the light output end thereof in the vicinity of the ultrasonic transducers.

Figure 6:
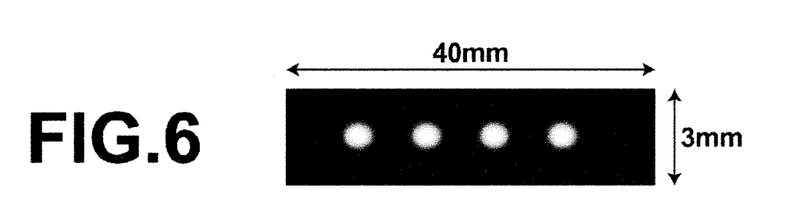
FIG. 6 is an image that illustrates the distribution of light at a boundary surface between a first light guiding portion and a second light guiding portion.

FIG. 6 is an image that illustrates the distribution of light at a boundary surface between the first light guiding portion 61 and the second light guiding portion 62. A light guiding plate 60 having a cross section with a width of 40 mm and a height of 3 mm will be considered. It is assumed that the fiber core diameters of the optical fibers 21 are 0.3 mm, and the fiber light output has a NA (Numerical Aperture) equivalent to 0.22. In addition, it is assumed that the refractive index of the first light guiding portion 61 is 1.45. FIG. 6 is an image that illustrates the distribution of light in the case that the length A of the first light guiding portion 61 is 12 mm. In other words, FIG. 6 illustrates the distribution of light at a cross section 12 mm remote from the light input end of the light guiding plate 60. The black portions in the image correspond to portions where the light is weak, and the white portions correspond to portions where the light is strong.

Figure 7:
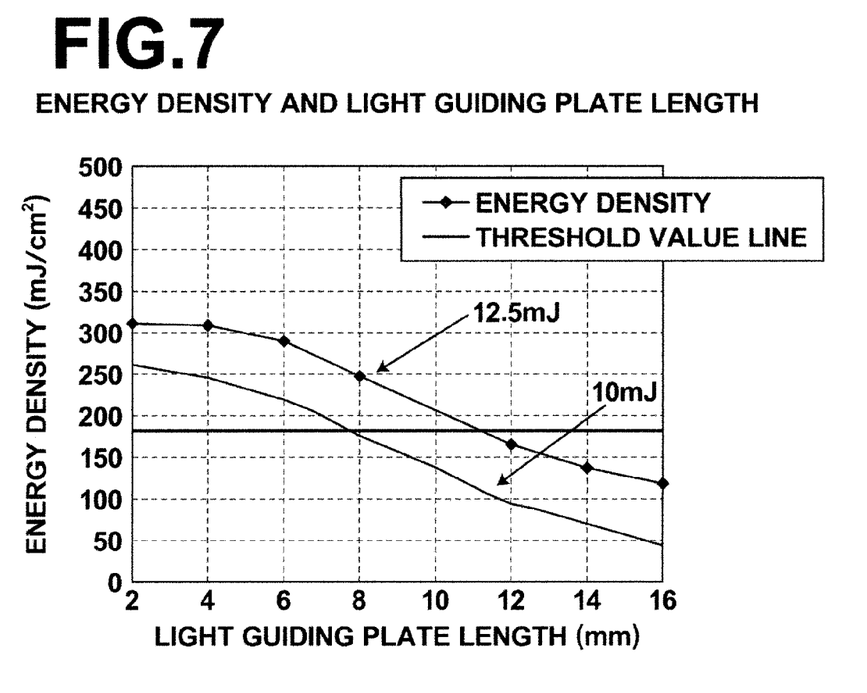
FIG. 7 is a graph that illustrates the relationship between the length of the first light guiding portion and the energy density of light at the boundary surface.

FIG. 7 is a graph that illustrates the relationship between the distance from the light input and the energy density of light. The horizontal axis of the graph represents the distance from the light input end to the boundary surface between the first light guiding portion 61 and the second light guiding portion 62, that is, the length of the first light guiding portion 61. The vertical axis represents the maximum value of the energy density of light (for example, the energy density at a portion in which the average energy density is highest within a 1 mm·1 mm region) at the boundary surface between the first light guiding portion 61 and the second light guiding portion 62. Cases were considered in which the energy input to the optical fiber is 12.5 mJ and 10 mJ. Referring to FIG. 7, it can be understood that the maximum values of the energy density of light become greater as the length of the first light guiding portion 61 becomes shorter. This is because the cross sectional area of light is smaller as the length of the first light guiding portion 61 is shorter.

Here, if the energy density of light that enters the second light guiding portion 62 is excessively high, there is a possibility that the resin, polycarbonate for example, that constitutes the second light guiding portion 62 will be damaged. It is known that resin will be damaged if light having an energy density of 180 mJ/cm$^2$ or greater enters thereinto, based on the heat resistance standards (temperature, etc.) of polycarbonate and experimental results. Referring to FIG. 7, cases in which the energy density at the boundary surface between the first light guiding portion 61 and the second light guiding portion 62 exceeds 180 mJ/cm$^2$ (threshold level) occur when the length of the first light guiding portion 61 is less than 11 mm in the case that the energy input into the optical fibers is 12.5 mJ, and when the length of the first light guiding portion 61 is less than 8 mm in the case that the energy input into the optical fibers is 10 mJ. It is desirable for the length of the first light guiding portion 61 to be 8 mm or greater, because energy which is practically capable of being input to the optical fibers is approximately 10 mJ. With respect to the length of the second light guiding portion 62, this length is not particularly limited, and may be selected as appropriate according to targets of measurement, etc.

A plurality of optical fibers are coupled to a single light guiding plate 60 in the present embodiment. Even in such a case, the same advantageous effects as those obtained by the first embodiment are obtained, because the light guiding plate 60 includes the first light guiding portion 61 formed by glass and the second light guiding portion 62 formed by resin. In addition, the energy density of light that enters the second light guiding portion 62 can be made lower than the threshold level by setting ht length of the first light guiding portion 61 to be 8 mm or greater, thereby preventing damage to the second light guiding portion 62.

Figure 8:
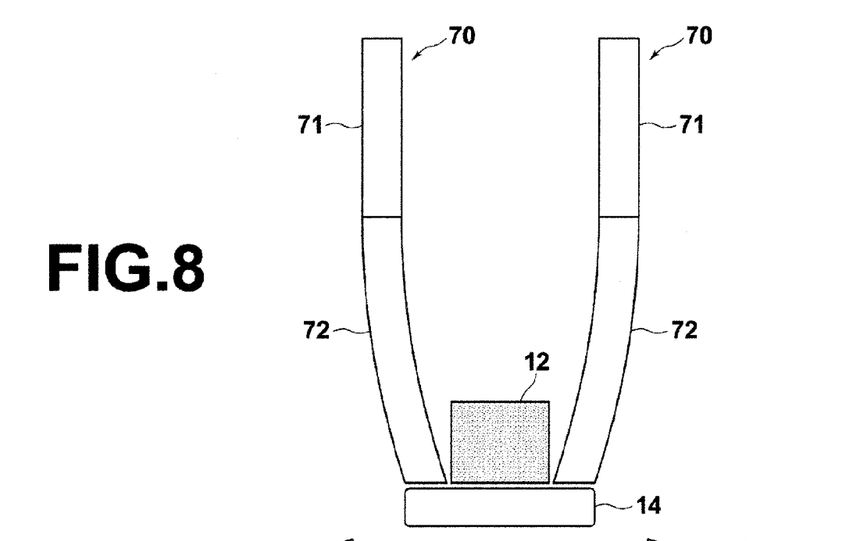
FIG. 8 is a sectional diagram of an ultrasound probe according to a third embodiment of the present invention in the lateral direction.

Next, a third embodiment of the present invention will be described. FIG. 8 is a sectional diagram of an ultrasound probe 10 according to the third embodiment of the present invention in the lateral direction. The ultrasound probe 10 is equipped with two light guiding plates 70 that face each other with the ultrasonic transducers 12 interposed therebetween. The light guiding plates 70 have first light guiding portions 71 formed by glass and second light guiding portions 72 formed by resin. The first light guiding portions correspond to the first light guiding portion 41 illustrated in FIG. 3 or the first light guiding portion 61 illustrated in FIG. 5. The second light guiding portions 72 correspond to the second light guiding portion 42 illustrated in FIG. 3 or the second light guiding portion 62 illustrated in FIG. 5. The second light guiding portions 72 are curved toward the ultrasonic transducers.

In the present embodiment, the ultrasound probe 10 is further equipped with an adapter 14, which is a resin gel adapter or the like. The adapter 14 has light transmitting properties and ultrasonic wave transmitting properties. The adapter 14 is mounted onto the ultrasound probe 10 so as to cover ultrasonic wave detecting surfaces of the ultrasonic transducers 12 and the light output surfaces of the light guiding plates 70. Light guided by the light guiding plates 70 is emitted onto a subject via the adapter 14. Light emission onto regions directly under the ultrasonic transducers, which are difficult to emit light onto, is facilitated by use of the adapter 14. The ultrasound probe of the third embodiment is the same as those of the first and second embodiments in the remaining points.

Figure 9:
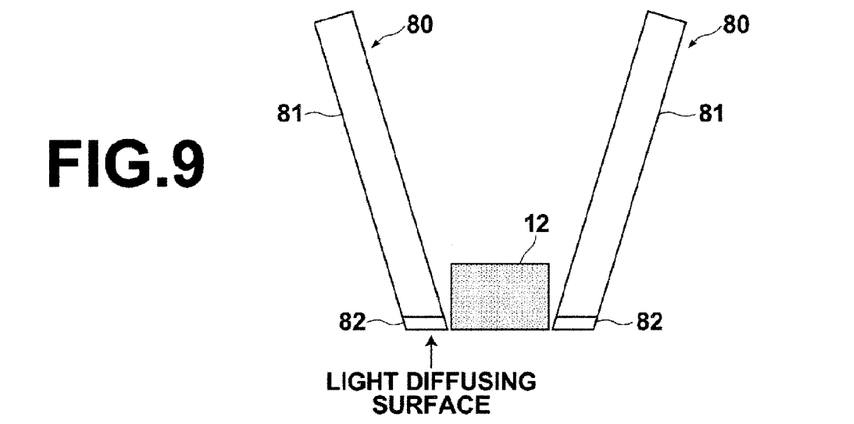
FIG. 9 is a sectional diagram of an ultrasound probe according to a fourth embodiment of the present invention in the lateral direction.

Next, a fourth embodiment of the present invention will be described. FIG. 9 is a sectional diagram of an ultrasound probe 10 according to the fourth embodiment of the present invention in the lateral direction. The ultrasound probe 10 is equipped with two light guiding plates 80 that face each other with the ultrasonic transducers 12 interposed therebetween. The light guiding plates 80 have first light guiding portions 81 formed by glass and second light guiding portions 82 formed by resin. The first light guiding portions correspond to the first light guiding portion 41 illustrated in FIG. 3 or the first light guiding portion 61 illustrated in FIG. 5. The second light guiding portions 82 correspond to the second light guiding portion 42 illustrated in FIG. 3 or the second light guiding portion 62 illustrated in FIG. 5.

Light diffusing surfaces are formed at the end surfaces of the second light guiding portions 82 toward the light output sides thereof. For example, protrusions and recesses that diffuse light are formed on the end surfaces of the second light guiding portions 82 toward the light output sides thereof. Light diffusing surfaces may be formed at the end surfaces of the second light guiding portions 82 toward the light input sides thereof (toward the boundaries thereof with the first light guiding portions 81) instead of or in addition to the light diffusing surfaces on the end surfaces toward the light output sides thereof. The need to provide separate light diffusing plates 13 (FIG. 2A and FIG. 2B) is obviated, by imparting the second light guiding portions 62 with the function of diffusing light.

In addition, in the present embodiment, the light guiding plates 80 are provided at predetermined angles with respect to the ultrasonic wave detecting surfaces of the ultrasonic transducers 12 such that the light output from the light guiding plates 80 will propagate in directions toward the interiors of the ultrasonic transducers 12, instead of forming the second light guiding portions to be curved toward the interiors of the ultrasonic transducers. By providing the light guiding plates 80 such that they are inclined in this manner, light can be emitted toward a direction directly under the ultrasonic transducers from the light output surfaces of the light guiding plates 80.

Figure 10:
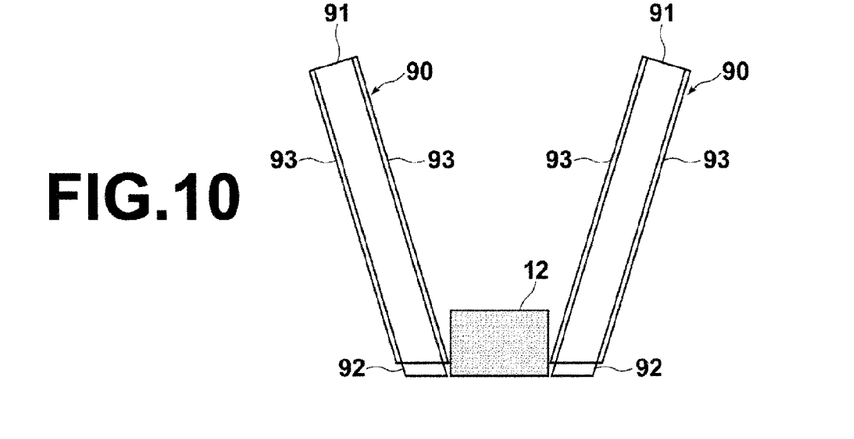
FIG. 10 is a sectional diagram of an ultrasound probe according to a fifth embodiment of the present invention in the lateral direction.

Next, a fifth embodiment of the present invention will be described. FIG. 10 is a sectional diagram of an ultrasound probe 10 according to the fifth embodiment of the present invention in the lateral direction. The ultrasound probe 10 is equipped with two light guiding plates 90 that face each other with the ultrasonic transducers 12 interposed therebetween. The light guiding plates 90 have first light guiding portions 91 formed by glass and second light guiding portions 92 formed by resin. The first light guiding portions 91 correspond to the first light guiding portion 41 illustrated in FIG. 3 or the first light guiding portion 61 illustrated in FIG. 5. The second light guiding portions 92 correspond to the second light guiding portion 42 illustrated in FIG. 3 or the second light guiding portion 62 illustrated in FIG. 5. Light diffusing surfaces may be formed on at least one of the end surfaces of the second light guiding portions 92 toward the light input sides and the light output sides thereof.

Each of the light guiding plates 90 includes a light transmitting portion that has light transmitting properties and reflecting members which are formed to sandwich the light transmitting portion therebetween. In FIG. 10, the first light guiding portions 91 correspond to the light transmitting portions, and reflective films 93 correspond to the reflecting members. Inorganic materials, aluminum, etc. may be employed as the material of the reflective films 93. The reflective films 93 are provided on the first light guiding portions 91 in FIG. 10. An alternate configuration, in which the reflective films 93 are provided on the second light guiding portions 92, may be adopted. Another alternate configuration, in which a material having a lower refractive index than that of the core light transmitting portions is provided to sandwich the core instead of sandwiching the core with the reflective members, may also be adopted. An organic material such as CYTOP may be employed as the material having the lower refractive index. Even if these configurations are adopted, light that enters the light guiding plates from the optical fiber can be prevented from leaking out from the lateral surfaces of the light guiding plates.

The present invention has been described above based on preferred embodiments. However, the ultrasound probe of the present invention is not limited to the above embodiments. Various changes and modifications to the above embodiments are included within the scope of the present invention.

What is claimed is:

1. An ultrasound probe, comprising:
    a plurality of ultrasonic transducers which are arranged along a predetermined direction;
    at least one optical fiber configured to guide light from a light source to one of at least one light guiding sections;
    each light guiding section configured to guide light from a light input end which is optically coupled with the at least one optical fiber to a light output end face provided next to ultrasonic wave transmitting and/or detecting surfaces of the ultrasonic transducers;
    each light guiding section including:
    a first plate shaped light guiding portion formed by a glass material that is of a rectangular shape in cross section having a width in the predetermined direction that is wider than a width in a direction perpendicular to the predetermined direction in the cross section, the first plate shaped light guiding portion including the light input end and is configured to guide light from the light input end toward the light output end face and enlarge a cross sectional area of input light at the light input end at an output end of the first plate shaped light guiding portion;
    a second plate shaped light guiding portion formed by a resin material that is of a rectangular shape in cross section having a width in the predetermined direction that is wider than a width in a direction perpendicular to the predetermined direction in the cross section, the second plate shaped light guiding portion being optically coupled with the output end of the first plate shaped light guiding portion and configured to guide light guided by the first plate shaped light guiding portion to an output end of the second plate shaped light guiding portion; and
    a light diffusing plate which is optically coupled with the output end of the second plate shaped light guiding portion and includes the light output end face, the light diffusing plate configured to diffuse light emitted from the second plate shaped light guiding portion toward a subject;
    wherein the ultrasonic wave transmitting and/or detecting surfaces of the ultrasonic transducers and the light output end face are positioned in the same plane; and
    wherein the first plate shaped light guiding portion includes a light guiding path formed in a tapered shape.

2. An ultrasound probe as defined in claim 1, wherein:
    the first plate shaped light guiding portion enlarges a width of guided light in the predetermined direction at the output end of the first plate shaped light guiding portion to be at least greater than a width of the input light in the predetermined direction at the light input end.

3. An ultrasound probe as defined in claim 1, wherein:
    the second plate shaped light guiding portion is curved in a direction toward the ultrasonic wave transitting and/or detecting surfaces.

4. An ultrasound probe as defined in claim 1, wherein:
    each light guiding section is provided inclined at a predetermined angle with respect to the ultrasonic wave transmitting and/or detecting surfaces of the ultrasonic transducers.

5. An ultrasound probe as defined in claim 1, wherein: the at least one optical fiber comprises a plurality of optical fibers and the at least one light guiding section comprises a plurality of light guiding sections.

6. An ultrasound probe as defined in claim 1, wherein:
    the at least one optical fiber comprises a plurality of optical fibers; and
    wherein the plurality of optical fibers are arranged along the predetermined direction and are optically coupled to the light input end.

7. An ultrasound probe as defined in claim 6, wherein:
    the at least one light guiding section comprises two light guiding sections; and the two light guiding sections are provided to face each other with the ultrasonic transducers interposed therebetween.

8. An ultrasound probe as defined in claim 1, wherein:
    each of the first plate shaped light guiding portion and the second shaped light guiding portion has a planar core and planar cladding layers provided on both surfaces of the planar core.

9. An ultrasound probe as defined in claim 1, wherein:
    each of the first plate shaped light guiding portion and the second plate shaped light guiding portion comprises a light transmitting portion having light transmitting properties and reflective members which are formed to sandwich the light transmitting portion therebetween.

10. An ultrasound probe as defined in claim 1, wherein:
    a distance from the light input end to a boundary between the first plate shaped light guiding portion and the second plate shaped light guiding portion is 8 mm.

11. An ultrasound probe as defined in claim 1, further comprising:
    an adapter which is formed by a material that transmits light and ultrasonic waves, the adapter being mounted to the ultrasound probe so as to cover the ultrasonic transducers and the light output end face.

12. An ultrasound probe as defined in claim 1, wherein the at least one light guiding section comprises a plurality of light guiding sections, and wherein the plurality of light guiding sections are arranged along a direction perpendicular to the predetermined direction.

* * * * *